United States Patent
Lynn et al.

(10) Patent No.: US 10,828,193 B2
(45) Date of Patent: Nov. 10, 2020

(54) FOOT PEDAL SYSTEM AND APPARATUS

(71) Applicant: Johnson & Johnson Surgical Vision, Inc., Santa Ana, CA (US)

(72) Inventors: Kyle Lynn, Tustin, CA (US); Tuan Tran, Garden Grove, CA (US); Christopher J. Page, Cambridge, MA (US); Allan Lee Cameron, Natick, MA (US); Andrew J. Boyce, Hopkinton, MA (US); Philip Walker, Concord, MA (US); Kelvin Kao, Long Beach, CA (US); Kenneth E. Kadziauskas, Coto de Caza, CA (US); Regan A. Pierce, Laguna Niguel, CA (US); Fred Lee, Irvine, CA (US); Teresita Smith, Lake Forest, CA (US); Tapan Patel, Chino Hills, CA (US)

(73) Assignee: Johnson & Johnson Surgical Vision, Inc., Santa Ana, CA (US)

(*) Notice: Subject to any disclaimer, the term of this patent is extended or adjusted under 35 U.S.C. 154(b) by 336 days.

(21) Appl. No.: 14/255,567

(22) Filed: Apr. 17, 2014

(65) Prior Publication Data
US 2014/0364864 A1    Dec. 11, 2014

Related U.S. Application Data

(60) Provisional application No. 61/814,097, filed on Apr. 19, 2013.

(51) Int. Cl.
*A61F 9/007* (2006.01)
*G05G 1/30* (2008.04)
(Continued)

(52) U.S. Cl.
CPC ......... *A61F 9/00745* (2013.01); *G05G 1/305* (2013.01); *A61B 2017/00973* (2013.01);
(Continued)

(58) Field of Classification Search
CPC ....... A61B 2017/00973; A61F 9/00745; A61F 9/007; A61F 9/00709; A61F 9/00718;
(Continued)

(56) References Cited

U.S. PATENT DOCUMENTS 1,399,054 A * 12/1921 Gewalt ................... G05G 1/30
  74/526
3,833,782 A *  9/1974 Bartel .................... H01C 10/16
  200/86.5

(Continued)

OTHER PUBLICATIONS

International Search Report and Written Opinion for Application No. PCT/US2014/034524, dated Jul. 8, 2014, 10 pages.

*Primary Examiner* — Wade Miles
*Assistant Examiner* — Kankindi Rwego
(74) *Attorney, Agent, or Firm* — Johnson & Johnson Surgical Vision, Inc.

(57) ABSTRACT

A phacoemulsification system and method, and a surgical foot pedal device, system and method. The present invention may include a console comprising a plurality of modes for at least one physically associated surgical instrument, and a foot pedal communicatively associated with said console and suitable for varying ones of the plurality of modes. The foot pedal may include a housing comprising the communicative association, and comprising at least one potentiometer and at least two top switches for the varying of the ones of the plurality of modes, a treadle rotatably mounted within the housing and suitable for depressing the at least one potentiometer, and at least two side switches movably associated with the treadle for the varying of the ones of the plurality of modes.

18 Claims, 9 Drawing Sheets

(51) Int. Cl.
*A61B 17/00* (2006.01)
*H01H 3/14* (2006.01)

(52) U.S. Cl.
CPC .......... *H01H 3/14* (2013.01); *H01H 2225/00* (2013.01); *H01H 2239/05* (2013.01); *H01H 2300/014* (2013.01)

(58) Field of Classification Search
CPC .............. A61F 9/00727; A61F 9/00736; A61F 9/00754; A61F 9/00763; A61F 9/00772; A61F 9/00781; G05G 1/30; G05G 1/305; G05G 1/38; G05G 1/40; G05G 1/405; G05G 1/48; G05G 1/483; G05G 1/55; G05G 1/60; H01H 3/14; H01H 13/16; H01H 21/26; H01H 2300/014; H01H 2239/05; H01H 2225/00; H01H 2225/002; H01H 2225/004; H01H 2225/006; H01H 2225/008; H01H 2225/01; H01H 2225/012; H01H 2225/014; H01H 2225/016; H01H 2225/018; H01H 2225/02; H01H 2225/022; H01H 2225/024; H01H 2225/026; H01H 2225/028; H01H 2225/03

USPC ...................................................... 200/86.5
See application file for complete search history.

(56) References Cited

U.S. PATENT DOCUMENTS

| | | | |
|---|---|---|---|
| 4,983,901 A | | 1/1991 | Lehmer |
| 5,091,656 A | | 2/1992 | Gahn |
| 5,157,603 A | * | 10/1992 | Scheller ............... A61B 17/32 604/22 |
| 5,554,894 A | | 9/1996 | Sepielli |
| 6,138,383 A | * | 10/2000 | Steinke ............... A43B 7/1425 36/141 |
| 6,360,630 B2 | | 3/2002 | Holtorf |
| 6,862,951 B2 | * | 3/2005 | Peterson ............... G05G 1/30 74/512 |
| 7,012,203 B2 | * | 3/2006 | Hanson ............... A61B 17/00 200/86.5 |
| 2004/0035242 A1 | | 2/2004 | Peterson et al. |
| 2008/0067046 A1 | | 3/2008 | Dacquay et al. |
| 2010/0198200 A1 | * | 8/2010 | Horvath ............... A61B 17/00 606/10 |
| 2011/0098721 A1 | | 4/2011 | Tran et al. |

\* cited by examiner

FOOT PEDAL SYSTEM AND APPARATUS

CROSS-REFERENCES TO RELATED APPLICATIONS

This application claims priority to U.S. provisional application No. 61/814,097 filed on Apr. 19, 2013, the entire contents of which is incorporated herein by reference.

TECHNICAL FIELD OF THE INVENTION

The present invention is generally related to methods, systems and apparatuses for controlling surgical aspects, particularly during treatment of an eye, and more particularly for controlling surgical aspects using a foot pedal.

BACKGROUND OF THE INVENTION

Ophthalmic surgical apparatuses, such as phacoemulsification apparatuses, typically include operating controls for regulating parameters or functions of the apparatuses. A phacoemulsification apparatus is particularly directed to the surgical removal of the natural, crystalline lenses from cataractic eyes, such as to allow for and/or prior to the insertion of an artificial intraocular lens.

Such an apparatus typically includes a console, power supply, one or more pumps as well as associated electronic hardware for operating a multifunction surgical implement to ultrasonically emulsify eye tissue, irrigate the eye with a saline solution and aspirate the emulsified lens from the eye. Typically, such surgical implements are handheld.

In view of the handheld nature of the instrumentation necessary for a phacoemulsification procedure, it is generally desirable that the hands of a surgeon remain as free as possible during performance of a surgery. Accordingly, foot controls, such as in the form of a mechanical foot pedal, are frequently provided in order to facilitate use of the handpiece by delegating other control functions to the foot pedal device.

Any number of foot pedal device systems have been utilized, and those utilized include a variety of pneumatic and electrical actuators to control an ophthalmic surgical apparatus. For instance, improved foot pedal control systems such as those described in U.S. Pat. No. 4,983,901 provide for a great number of control variations and modes for operating phacoemulsification apparatus. One popular type of foot control is termed a dual-control foot pedal because of the two directions of foot movement available to actuate the controls. For example, in a dual-control pedal, a treadle (the actual pedal) may be pivoted in a vertical plane (pitch), as in a standard car accelerator-type pedal, while also being rotated in a horizontal plane, or yaw, direction. In addition to the dual treadle control, one or more other foot-actuated switches placed close to the treadle are often provided for easy access.

The foot pedal must be user friendly in order to provide a surgeon comfort and reliability in its use, so as not to initiate disruption of the surgeon's concentration when performing surgery. For example, during control of the foot pedal the surgeon's posture is influenced by efforts to prevent losing contact with the foot pedal, which is typically achieved by keeping one foot flexed above the pedal and loading the body weight on the other foot. This causes a non-ergonomic posture which can lead to physical discomfort, and sometimes mistakes in control of the foot pedal.

Furthermore, as may be expected, different types of foot pedals are preferred by different surgeons, with some surgeons preferring an accelerator-type pedal in which the sole of the surgeon's foot is utilized for depression, while others desire a pedal engageable by the surgeon's toe in order to depress the pedal. This, of course, has led to the development of a multitude of foot pedal devices of diverse configuration in order to provide the comfort and reliability desired by individual surgeons. For instance, U.S. Pat. No. 6,360,630 to Holtorf discloses a dual position foot pedal rotatably mounted to a base in order to be operated by the toe or sole of a user's foot. However, even with such flexible designs, a change in foot pedals is often required when a phacoemulsification apparatus is utilized in sequence by different physicians, which is inconvenient and may require recalibration of the apparatus. In addition, such alternative foot pedals may not be available or even offered by a manufacturer.

Despite the availability of a number of relatively effective foot pedal designs, there is a need for a more ergonomically flexible foot pedal that enhances surgeon comfort and concentration.

SUMMARY OF THE INVENTION

The present invention provides at least phacoemulsification system and method, and a foot pedal device, system and method. The present invention may include a console comprising a plurality of modes for at least one physically associated surgical instrument, and a foot pedal communicatively associated with said console and suitable for varying ones of the plurality of modes. The foot pedal may include a housing comprising the communicative association, and comprising at least one potentiometer and at least two top switches for the varying of the ones of the plurality of modes, a treadle rotatably mounted within the housing and suitable for depressing the at least one potentiometer, and at least two side switches movably associated with the treadle for the varying of the ones of the plurality of modes.

The invention may further include the foot pedal comprising a heel loop adjacent to a heel-receiving portion of the treadle. The treadle may further comprise a heel cup portion for receiving a user's heel. The heel cup portion may comprise an elastomer.

Moreover, the side switches may be undercut with respect to a portion of the housing comprising the top switches. Further, the side switches may be curvilinear.

BRIEF DESCRIPTION OF THE DRAWINGS

The present invention is best understood with reference to the following detailed description of the invention and the drawings, in which.

DETAILED DESCRIPTION OF THE INVENTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined herein.

Figure 1:
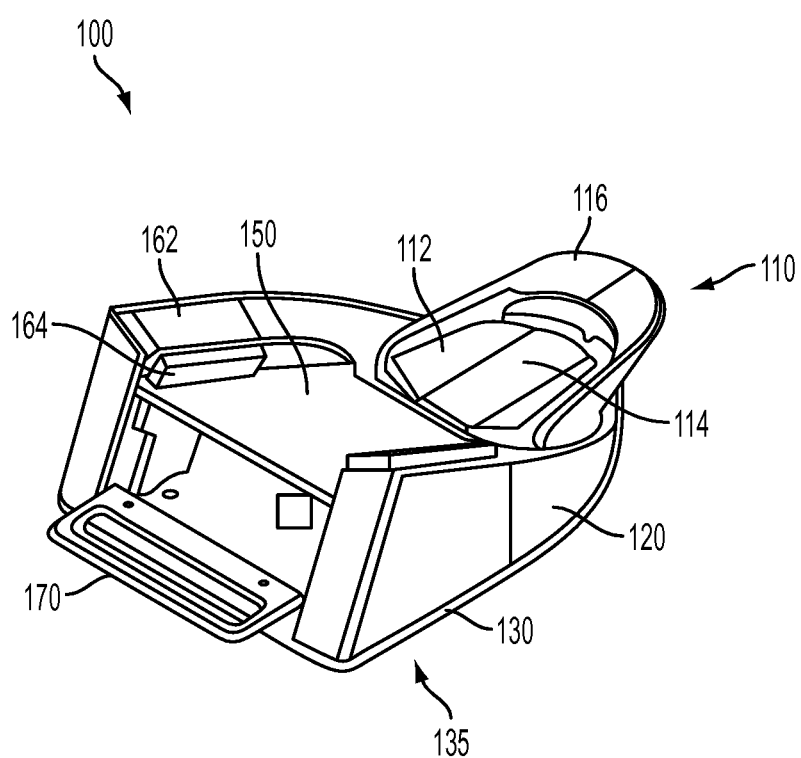
FIG. 1 illustrates a prospective view of a foot pedal control for use in the system of FIG. 6.

FIG. 1 is a prospective view of an exemplary foot pedal control 100 for use in a surgical system, for instance during an ophthalmic surgery. The foot pedal control 100 comprises a base 130 on which is mounted body housing 120, a treadle 150, a heel cup assembly 110, and an optional carrying handle 170. The base 130 has an undercarriage 135 arranged to lie flat on a ground surface. More specifically, the undercarriage 135 includes either a flat bottom surface or a series of separate feet that may provide a stable base surface on the ground. The base may provide improved stability in undercarriage embodiments including a gripping surface, such as rubber, rubberized, plastic, or like traction strips or treads (not shown).

For purposes of orientation, the foot pedal control 100 extends upward from the base 130, a forward or anterior direction is to the left in FIG. 1 and a rearward or posterior direction is to the right. Furthermore, in an embodiment the treadle 150 is symmetric about a vertical medial plane bisecting the treadle into two substantially symmetric lateral (left and right) halves. The various components of the foot pedal control 100 may be made from any suitable material, such as stainless steel, titanium, or plastic. In an exemplary embodiment, the treadle 150 and heel loop 116 may comprise at least one metal and the housing 120 may comprise carbon-plastic.

Top switch assemblies 162 may be suitably and actuatably mounted on the body housing 120. In embodiments, side switches 164 may be suitably and actuatably mounted to, and/or movably associated with, treadle 150.

The heel cup assembly 110 may include an upper portion comprising a heel loop 116 and a lower portion comprising an upper heel cup portion 112 and a lower heel cup portion 114. The heel loop 116 may be substantially rigid and may or may not be static during use of foot pedal control 100. Further, the heel loop may be adjustable, such as by allowing for an increase or decrease in the lateral distance from the rearmost point of the heel loop 116 and the frontmost portion of the pedal.

The lower portion of heel cup assembly 110 may provide at least one angular portion to contact at least a portion of the side of a user's heel. For example, upper heel cup portion 112 may be angled and/or raised above lower heel cup portion 114 such that an object at rest of upper heel cup portion 112 may move towards lower heel cup portion 114 under the force of gravity. The heel cup portion may provide for ergonomic and comfortable receiving of the user's heel, and as such may be formed of an elastomeric material.

As referenced, the heel loop 116 may be adjustable and may be moved along the anterior-posterior axis to allow for various foot/heel sizes. Similarly, both upper heel cup portion 112 and a lower heel cup portion 114 may be adjustable and may, for example, have their angle relative to each other changed by the user to conform more suitably with the user's heel. The heel cup assembly 110 may also be customizable and may be interchangeable. Further, in an embodiment of the present invention, both upper heel cup portion 112 and a lower heel cup portion 114 may be adjustable independently from heel loop 116. The heel loop 116 may be affixed to or integrally formed with the base 130, for example, to allow for more easy interchangeability of both upper heel cup portion 112 and a lower heel cup portion 114. For example, a variety of heel cup assemblies may be provided to accommodate various foot sizes, shapes and/or desired support and may be inserted into foot pedal control 100 on a user-by-user basis.

Heel loop 116 may also be used as a handle for moving foot pedal control 100 and as a resting place for the foot, providing a portion of the foot pedal control 100 on which a user's foot may rest away from active portions of the foot pedal control 100 such as, for example, one of the two switches 162. More particularly, the heel loop may provide, for example, a carrying handle in embodiments in which the loop is not adjustable, in embodiments in which the adjustability of the heel loop may be locked, and in embodiments in which the handle 170 is removed and/or is not connected to the foot pedal control 100.

Yet further, the heel loop may accordingly allow for a user to make fine adjustments in the position of the foot pedal. For example, a user may raise her heel against a portion of the heel loop, thereby lifting the heel loop slightly, and, accordingly, thereby slightly raising the rearmost portion of the foot pedal to allow for positional adjustment of the pedal. Further detail on such embodiments is provided below.

Figure 2:
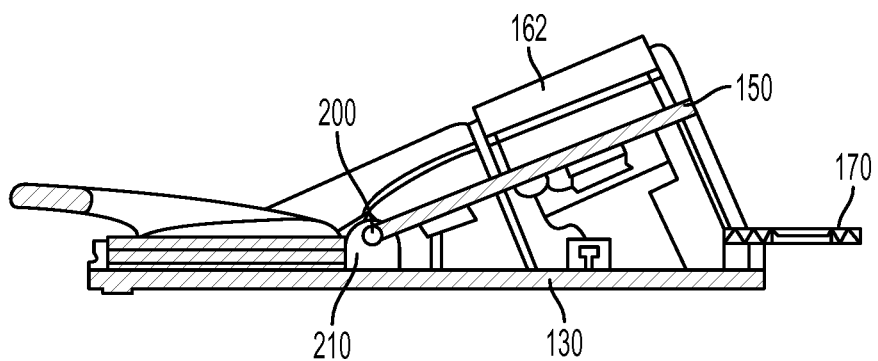
FIG. 2 illustrates a cross sectional view of an exemplary a foot pedal control.

FIG. 2 illustrates a section view of the foot pedal control 100 and is shown orientated with the anterior on the right and the posterior of foot pedal control 100 on the left. The base 130 may have attached thereto a holder assembly 210 which may receive and provide support for a pin associated with treadle 150. The pin may pass through the posterior end of the treadle 150 and may be perpendicular to the anterior-posterior axis of the foot pedal control 100. The pin passing through the treadle 150 may engage at least one holder assembly 210 and may engage at least one potentiometer 200, and may be statically engaged with treadle 150.

As pressure is exerted on treadle 150, treadle 150 may rotate about the linear axis of the pin and may cause the potentiometer 200 to rotate and/or be depressed, thereby generating an electrical signal correspondent to the resistance change which is itself correspondent to the distance traveled by the treadle 150 at its anterior end. The signal generated by the potentiometer 200 may be received by the surgical console and may allow a program run on the console to determine the position of the treadle 150. In this way, the user may control different modes and/or functionality provided through the surgical console. As explained in greater detail below, such modes and functionalities associated with various treadle positions may be customizable. The signal from the potentiometer 200 may be received by an encoder to provide a control signal to the surgical console. The encoder (not shown) may be included in the foot pedal control 100 and may communicate with the surgical console in various ways as described below.

Figure 3A:
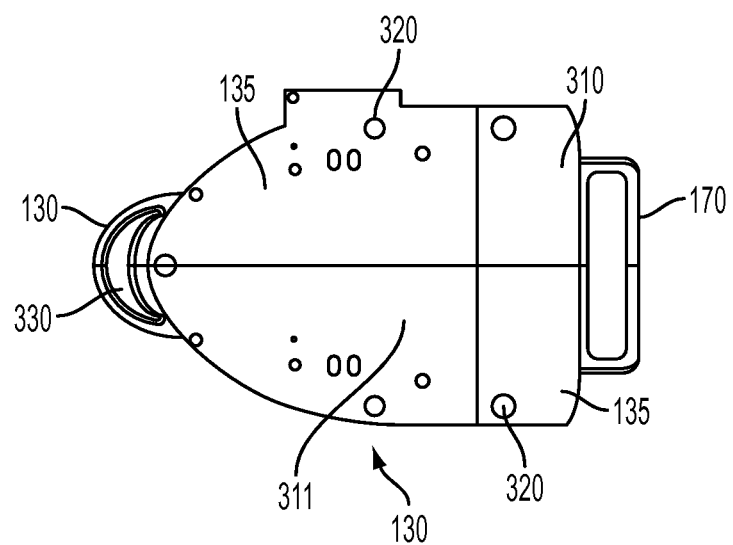
FIG. 3A illustrates a bottom view of an exemplary a foot pedal control.

As illustrated in FIG. 3, the base 130 and, more specifically, the undercarriage 135 may include at least two portions 310 and 311. Portion 310 may comprise a material having a lower friction coefficient than the material of portion 311 to allow for the foot pedal control 100 to be more easily moved when tipped forward in part by substantially limiting contact with the ground by portion 310. For example, a user may raise the posterior end of the foot pedal control 100 using one's toes on the bottom portion of heel loop 116, and may thereby maneuver the foot pedal control 100 by sliding substantially on portion 310. Although any number of low friction materials may be used, portion 310 may preferably comprise Teflon® and/or Teflon® like materials to allow for portion 310 to readily slide, such as when only portion 310 is frictionally in contact with the floor. Of course, portion 310 may comprise any material suitable for the undercarriage of a surgical foot pedal, and may be partially a high friction surface and partially the aforementioned low friction surface. For example, portion 310 may include rubber and/or rubberized plastics.

The foot pedal control 100 may be moved by hand or foot and may be preferably moved utilizing handle 170 and/or recess 330. Although either may be grasped by the hand, recess 330 of heel loop 116 may be best utilized by the toe(s) of a user and may allow for positioning of the foot pedal control 100 by a user's foot. For example, a user my insert at least one toe into the recess 330 and raise the foot pedal control 100 off the ground at an angle sufficient to allow the foot pedal control 100 to slide along the floor substantially on portion 310. As would be appreciated by those skilled in the art, the movement of the foot pedal control 100 may be forward and backwards and side to side as may be allowable by pivoting the foot pedal control 100 from recess 330.

Figure 3B:
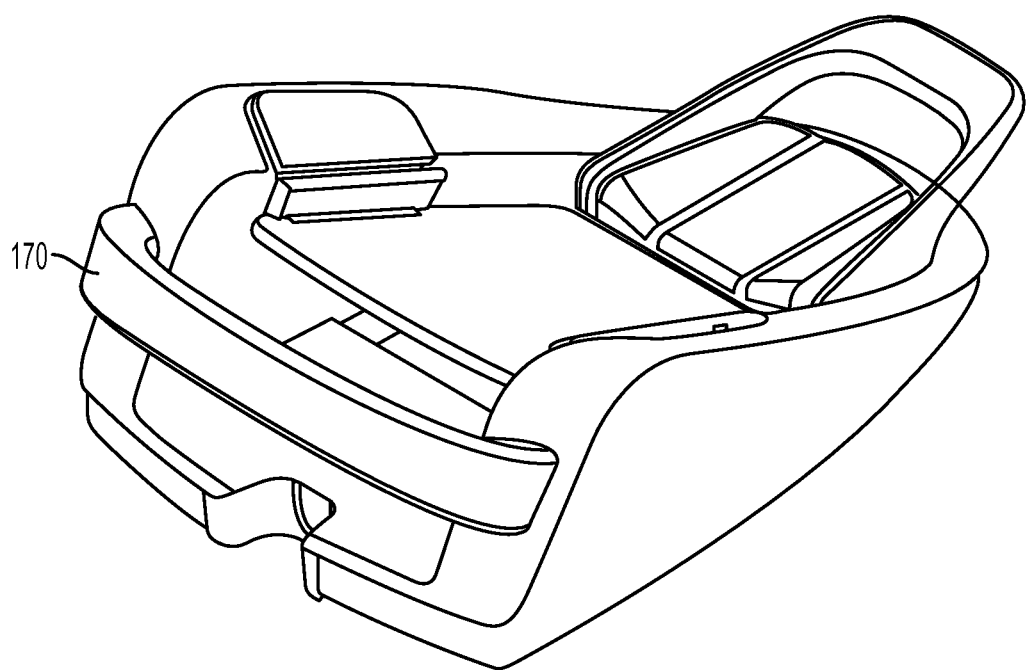
FIG. 3B illustrates a prospective view of an exemplary a foot pedal control.

Although handle 170 may be used by the foot of a user, it is preferably used by the hand of the user and may be removable so as to, for example, prevent interference with the use of foot pedal control 100. As illustrated in FIG. 3B, alternative embodiments of handle 170 may be employed. For example, the handle 170 may be attached to the posterior end of the housing 120 and may be located above the base 130. As discussed above, in this embodiment handle 170 may similarly be removable and/or may be attached in various locations on the housing 120 and/or base 130.

At least one foot 320 may be included in the base 130 and/or the undercarriage 135. Foot 320 may be composed of a high friction and/or non-slip material, such as a rubber, to prevent the foot pedal control 100 from inadvertently moving. Foot 320, if located in portion 310, may be composed of the same material as a foot 320 located in portion 311 or of a material having a smaller coefficient of friction than a foot 320 located in portion 311. Although the foot 320 is illustrated as a round object in FIG. 3, for example, foot 320 may be of any shape and may for example, comprise a larger area of undercarriage 135.

Figure 4A:
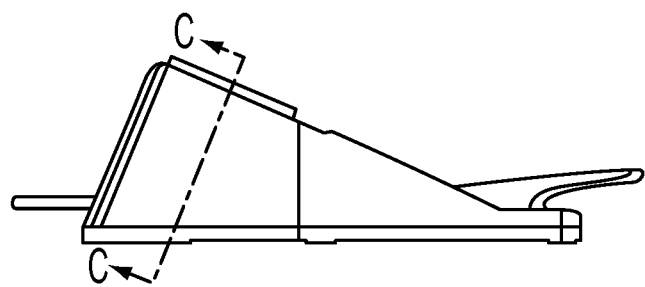
FIG. 4A illustrates a side view of an exemplary a foot pedal control.
Figure 4B:
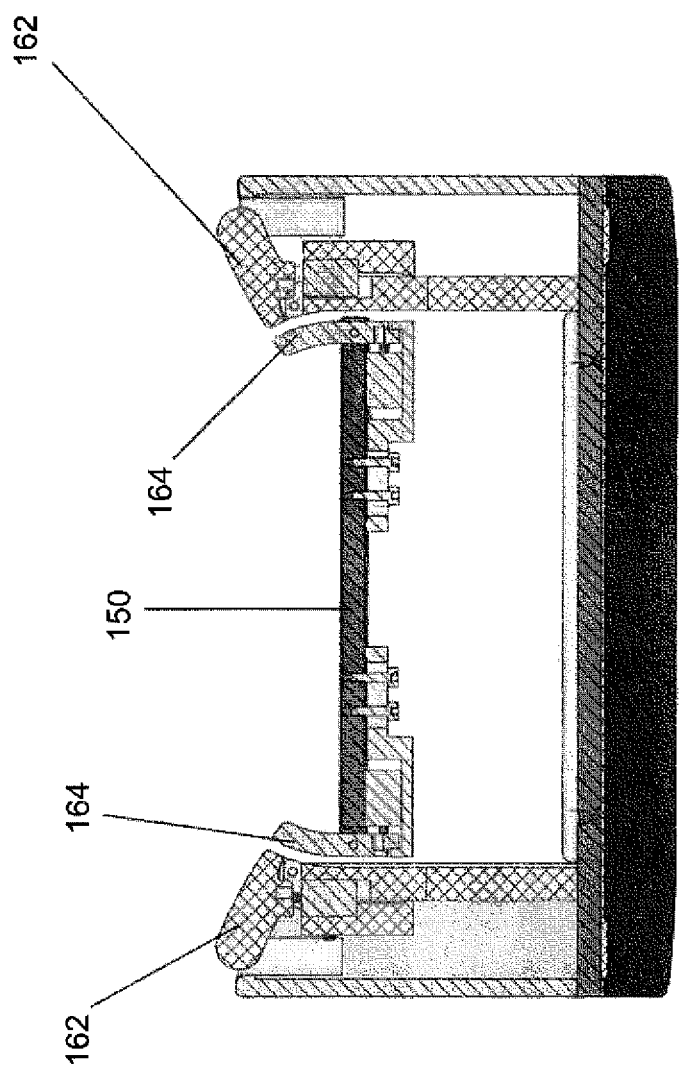
FIG. 4B illustrates a cross sectional view of an exemplary a foot pedal control.

FIG. 4A is a side view of foot pedal control 100 showing the dissection used for the front dissection view illustrated in FIG. 4B. As illustrated in FIG. 4B, the top switch assemblies 162 may be affixed to housing 120 and may not engage treadle 150. Top switch assembly 162 may be activated by any part of the user's foot and may be preferably activated by the underside of a user's foot by depressing the movable portion of the switch assembly 162 towards the base 130 of foot pedal control 100. Side switch assemblies 164 may be affixed to the treadle 150 and/or otherwise movably associated with treadle 150, may be activated by any part of the user's foot, and may be preferably activated by the side of a user's foot by depressing the movable portion of the switch assembly 164 towards the housing 120 of foot pedal control 100. The side switch assemblies 164 may be connected with at least one PCB (Printed Circuit Board), which may interface to a main connect, such as may be communicatively connected to the console, at or near the front portion of the pedal, such as through cabling under treadle 150. The cabling under the treadle 150 may comprise waterproof housing and may be sealed at points of intersection and connection with other aspects of foot pedal control 100 to maintain the overall waterproof nature of foot pedal control 100.

Side switch assemblies 164 may include at least one curved portion suitable for providing a receiving area for a portion of the user's foot. More particularly, the curvilinear portion may allow for the at least partial surrounding/receiving of at least a portion of the side of a user's foot. For example, a user may slide her right foot to the right side of the treadle 150 to engage the curved portion of the right side switch assembly 164. The curved portion may allow the user to feel engagement with side switch assembly 164 without activating the function provided by the switch. Accordingly, the instant side switches may assist in avoiding accidental actuation of the side switches.

When the treadle 150 is in the rest position, as illustrated in FIG. 4B, the top of side switch assembly 164 may be recessed below the top of top switch assembly 162 and may preferably be level with the top planar surface of top switch assembly 162 accessible by the user. As illustrated in FIG. 4B, top planar surface of top switch assembly 162 accessible to the user may be angled towards the treadle 150 to provide easier access by the user and to be more ergonomically situated. The undercut positioning of side switch assembly 164 as compared to top switch assembly 162 may prevent accidental and/or unwanted activation of a particular switch and may provide the user with increase tactile awareness of the position of the desired switch.

Each of the top switch assemblies 162 and side switch assemblies 164 may be programmable to control different functions performed through, for example, the surgical console. Similarly, treadle 150 may be programmed to perform various functionalities, and/or provide various modes and/or sub-modes, based on the position of treadle 150 relative to a designated starting position, and additionally based on the actuation of the top and side switches. For example, the starting position of treadle 150 may be designated as the upper most position as illustrated in FIG. 1 with at least two, three, or more additional positions delineated by, for example, preprogrammed correspondence or by the user. For example, the third position in a three position embodiment may be the lowest position of the treadle 150 with the reaming two positions located between the upper and lowest positions and roughly spaced between those positions.

Each position may be reached through depression of the treadle 150 by, for example, a user's foot, and may be visually indicated on at least one graphical user interface (GUI) of the console associated with the foot pedal control 100. Further, each position may have associated therewith a tactile, audio and/or motion alert to allow the user to accurately position treadle 150. For example, such an alert may take the form a sound from the foot pedal control 100 and/or the console, or may be indicated by a vibration provided by the foot pedal control 100 or the potentiometer, which alert may be communicatively received by the user.

The programmable positions of the treadle 150 may control different functions provided by the console and may be additive in nature. For example, a first position may be programmed to provide an irrigation function, a second position may add an aspiration and irrigation function, and a third position may add an ultrasound function to the aspiration and irrigation function. In addition, as discussed herein, the top switches 162 and side switches 164 may allow for control of the functions activated via the treadle 150. For example, if an aspiration function is activated via the treadle 150, at least one side switch 164 may be programmed to control the strength of the vacuum applied. Similarly, at least one top switch 162 may control which function is otherwise controlled by the treadle 150. For example, a top switch 164 may be programmed to toggle the treadle 150 functionality between aspiration only and a mix of aspiration and irrigation as described above. In another example, a top switch 164 may be programmed to toggle through preprogrammed surgical modes or submodes.

Figure 5A:
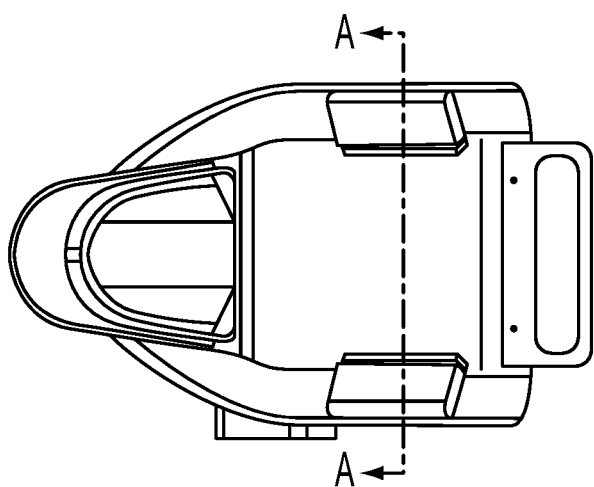
FIG. 5A is a top view of an exemplary foot pedal of the present invention.
Figure 5B:
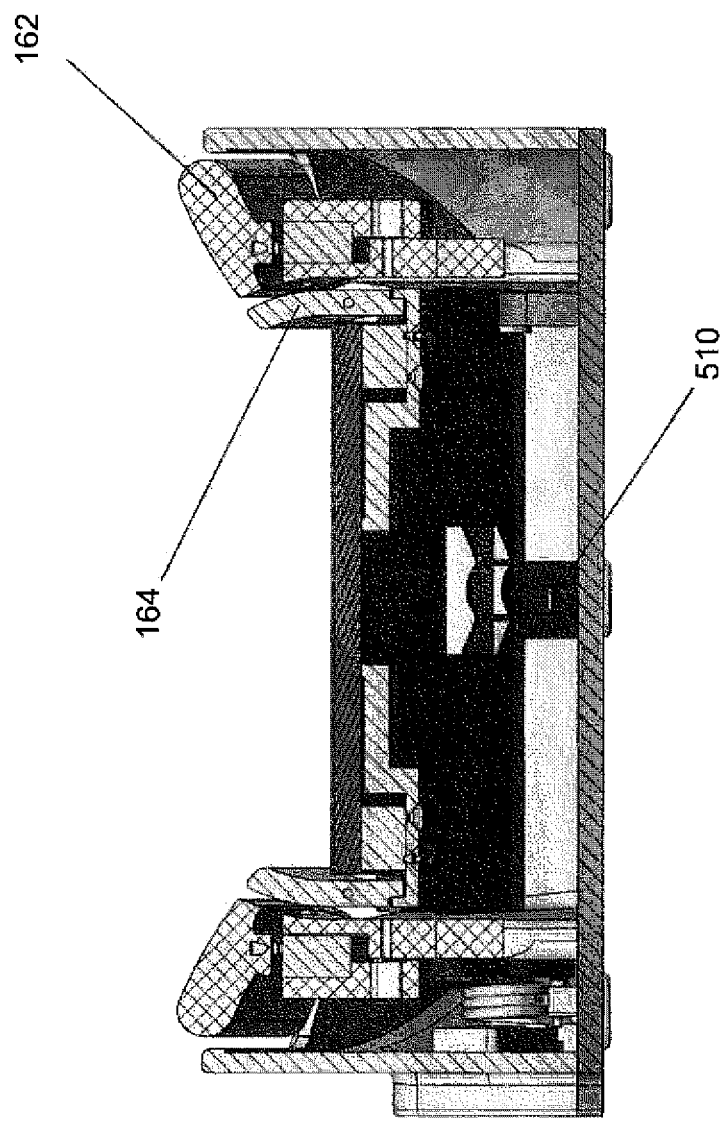
FIG. 5B illustrates a cross sectional view of an exemplary a foot pedal control.

FIG. 5A illustrates a top view of foot pedal control 100. FIG. 5B is a cross sectional view of foot pedal control 100 divided as illustrated in FIG. 5A and looking towards the posterior end of foot pedal control 100. In addition to the other features already described herein, a treadle stop 510 may be included. In an embodiment of the present invention, the treadle 150 may generally be of a rectangular shape and may extend to about the top switches 162. In an alternative embodiment, the treadle 150 may be generally of a triangular shape with the base of the triangle deposed at the anterior end of the foot pedal control 100 to proximately locate side switches 164 to top switches 162.

The foot pedal control 100 may be powered by a battery source and may include a rechargeable battery. As may be appreciated by those skilled in the art, a charging station may be used to recharge a rechargeable battery and may be incorporated in the associated console, for example. Similarly, if the foot pedal control 100 is hard wired to the console, such a linkage may provide any necessary power. As with the foot pedal control 100 as a whole, any battery and/or battery compartment may be sufficiently sealed to provide a waterproof system.

Figure 6:
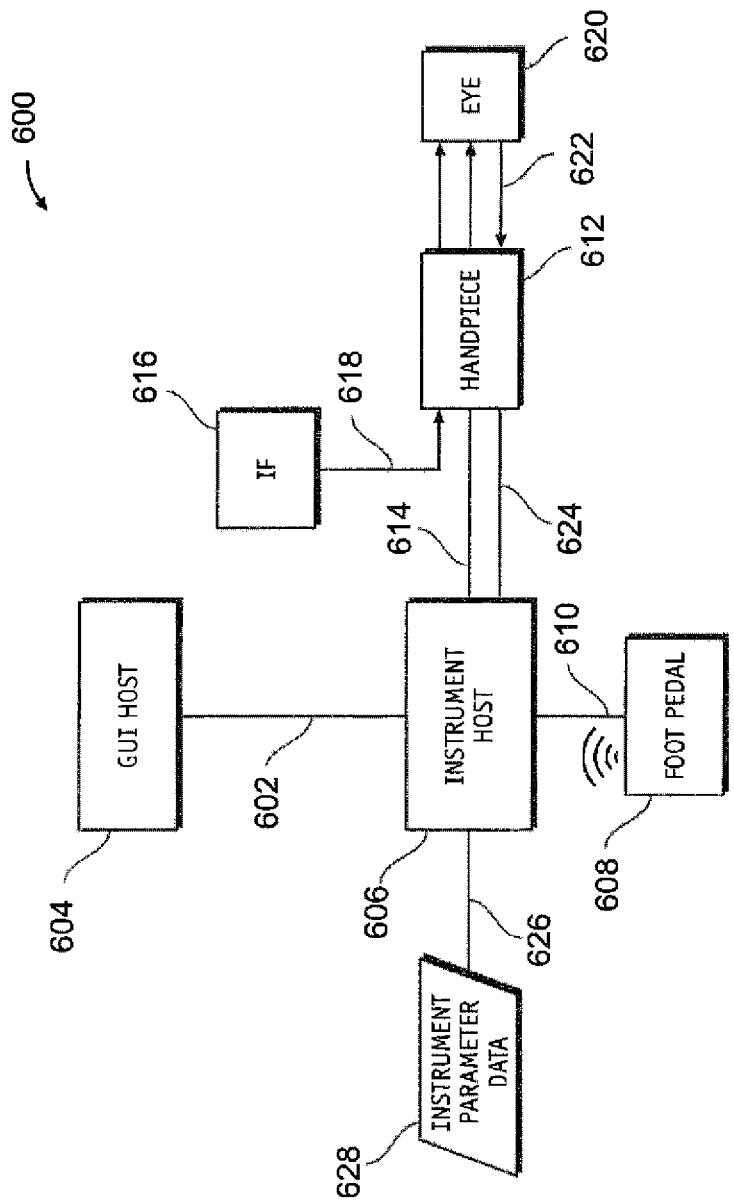
FIG. 6 is a schematic of an exemplary system in which a foot pedal control may operate.

While the present foot pedal control may be used in various environments and applications, a particularly useful application is in an ocular surgical system such as a phacoemulsification/vitrectomy system. For instance, FIG. 6 illustrates an exemplary phacoemulsification/vitrectomy system 600 in a functional block diagram to show the components and interfaces for a safety critical medical instrument system in which the foot pedal control disclosed herein may be utilized.

A serial communication cable 602 may connect a GUI 604 and instrument host 606 for the purposes of controlling the surgical instrument host 606 by the GUI host 604. The instrument host 606 may be considered a computational device in the arrangement shown, but other arrangements are possible. A switch module associated with an exemplary foot pedal 608, such as described herein, transmits control signals relating internal physical and virtual switch position information as input to the instrument host 606 over a serial communications cable 610, or wirelessly if desired. Instrument host 606 may provide a database file system for storing configuration parameter values, programs, and other data saved in a storage device (not shown). In addition, the database file system may be realized on the GUI host 604 or any other subsystem (not shown) that could accommodate such a file system.

The system 600 has a handpiece 612 that typically includes a needle and electrical means, such as a piezoelectric crystal, for ultrasonically vibrating the needle. The instrument host 606 supplies power on line 614 to the operative tip 612. An irrigation fluid source 616 can be fluidly coupled to operative tip 612 through line 618. The irrigation fluid and ultrasonic power are applied by the operative tip 612 to an eye 620, or other affected area or region. Alternatively, the irrigation source may be routed to the eye 620 through a separate pathway independent of the handpiece. Aspiration is provided from the eye 620 by one or more pumps (not shown), such as a peristaltic pump and/or venturi pump, via the instrument host 606, through lines 622 and 624. A surgeon/operator may select an amplitude of electrical pulses either using the handpiece, via the instrument host and GUI host, using the foot pedal, and/or voice command.

An interface communications cable 626 connects to the instrument host 606 for distributing instrument sensor/parameter data 628, and may include distribution of instrument settings and parameter information, to other systems, subsystems and modules within and external to instrument host 606. Although shown connected to the instrument host 606, interface communications cable 626 may be connected or realized on any other subsystem (not shown) that could accommodate such an interface device able to distribute the respective data.

While the invention has been described in its preferred embodiments, it is to be understood that the words which have been used are words of description and not of limitation. Therefore, changes may be made within the appended claims without departing from the true scope of the invention.

All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

The invention claimed is:

1. A phacoemulsification system, comprising:
a console comprising a plurality of modes for at least one physically associated surgical instrument; and
a foot pedal communicatively associated with said console and suitable for varying ones of the plurality of modes, said foot pedal comprising:
a housing comprising the communicative association,
at least one potentiometer, and at least two top switches for the varying of the ones of the plurality of modes, wherein the at least two top switches are affixed to said housing; and
a treadle rotatably mounted within the housing and suitable for actuating the at least one potentiometer, the treadle further comprising at least two side switches affixed to and movably associated with said treadle for the varying of the ones of the plurality of modes, wherein the at least two side switches have a bottom portion and a top portion, wherein the bottom portion is coupled with the treadle, and wherein the at least two side switches are curvilinear to surround at least a portion of a side of a user's foot from the treadle to the top portion of the at least two side switches.

2. The phacoemulsification system of claim 1, the housing further comprising a handle.

3. The phacoemulsification system of claim 1, wherein the at least two side switches are positioned below a portion of the at least two top switches.

4. The phacoemulsification system of claim 1, said foot pedal further comprising a heel loop adjacent to a heel-receiving portion of the treadle.

5. The phacoemulsification system of claim 4, an underside of the housing comprising a low friction surface suitable to allow movement of the housing upon a lifting of the heel loop.

6. The phacoemulsification system of claim 4, wherein the heel loop is adjustable.

7. The phacoemulsification system of claim 1, the foot pedal further comprising a heel cup portion for receiving a user's heel.

8. The phacoemulsification system of claim 7, the heel cup portion comprising an elastomer.

9. The phacoemulsification system of claim 7, wherein the heel cup portion is interchangeable.

10. A foot pedal, comprising:
   a housing;
   a treadle rotatably mounted within the housing and suitable for actuating at least one potentiometer;
   at least two side switches affixed to and movably associated with said treadle, wherein the at least two side switches have a bottom portion and a top portion, wherein the bottom portion is coupled with the treadle, and wherein the at least two side switches are curvilinear to surround at least a portion of a side of a user's foot from the treadle to the top portion of the at least two side switches;
   at least two top switches affixed to said housing; and
   a stationary heel cup immediately adjacent to said treadle, mounted to said housing, and suitable for receiving a heel of the user's foot;
   wherein one of the at least two side switches and at least two top switches variably control at least one of a plurality of modes associated with a surgical console.

11. The foot pedal of claim 10, wherein the housing comprises a low friction surface suitable to allow movement of the housing upon a lifting of a heel loop.

12. The foot pedal of claim 10, wherein the heel cup comprises an elastomer.

13. The foot pedal of claim 10, wherein the at least two side switches are positioned below a portion of the at least two top switches.

14. The foot pedal of claim 10, wherein the heel cup is interchangeable.

15. The foot pedal of claim 10, wherein the actuation of a potentiometer of the at least one potentiometers corresponds to at least one alert.

16. The foot pedal of claim 10, wherein the surgical console is suitable for use with phacoemulsification.

17. The foot pedal of claim 10, wherein said treadle is rotatably mounted about a parallel axis.

18. The foot pedal of claim 17, wherein the parallel axis is located approximate to the median of said treadle.

* * * * *